United States Patent [19]

Green

[11] Patent Number: 4,492,232

[45] Date of Patent: Jan. 8, 1985

[54] SURGICAL CLIP APPLYING APPARATUS HAVING FIXED JAWS

[75] Inventor: David T. Green, Norwalk, Conn.

[73] Assignee: United States Surgical Corporation, Norwalk, Conn.

[21] Appl. No.: 429,249

[22] Filed: Sep. 30, 1982

[51] Int. Cl.³ .............................................. A61B 17/12
[52] U.S. Cl. .................................... 128/325; 128/346; 227/DIG. 1
[58] Field of Search ............... 128/322, 346, 325, 326, 128/337; 227/DIG. 1; 29/243.56; 72/410; 24/255 SL; 206/339, 340; 251/10

[56] References Cited

U.S. PATENT DOCUMENTS

| | | |
|---|---|---|
| 1,514,259 | 11/1924 | Peters . |
| 2,140,593 | 12/1938 | Pankonin ............................ 206/340 |
| 2,222,726 | 11/1940 | Sorenson ............................ 206/340 |
| 2,242,502 | 5/1941 | Bangs ........................................ 59/35 |
| 2,359,574 | 10/1944 | Maskrey ................................. 1/49.1 |
| 2,758,302 | 8/1956 | White ....................... 227/DIG. 1 X |
| 3,079,608 | 3/1963 | Babkin ..................................... 1/187 |
| 3,584,347 | 6/1971 | Klenz ............................... 24/30.5 W |
| 3,584,628 | 6/1971 | Green .................................... 128/305 |
| 3,653,117 | 4/1972 | Wolfberg et al. ..................... 29/429 |
| 3,683,927 | 8/1972 | Noiles ............................ 128/334 R |
| 4,275,813 | 6/1981 | Noiles ...................... 227/DIG. 1 X |
| 4,361,229 | 11/1982 | Mericle ................................ 206/339 |
| 4,380,238 | 4/1983 | Colucci et al. ..................... 128/346 |

FOREIGN PATENT DOCUMENTS 2088723 6/1982 United Kingdom ............... 128/325

Primary Examiner—Michael H. Thaler
Attorney, Agent, or Firm—Robert R. Jackson; John E. Nathan

[57] ABSTRACT

Surgical clip applying apparatus having a pair of laterally spaced fixed jaws with opposing clip forming surfaces which are inclined toward one another in the direction in which a clip is pushed into the jaws. Tissue to be clipped is positioned between the jaws. A clip is pushed into the jaws so that the free end of each arm of the clip contacts a respective one of the clip forming surfaces, and so that the clip forming surfaces cooperate to force the arms of the clip together on opposite sides of the tissue to produce hemostasis of the tissue. Various means can be included in the apparatus for feeding a plurality of clips to the jaws one at a time in succession. The clips can be made of metal or of plastic. Plastic clips can be either biologically absorbable or nonabsorbable.

19 Claims, 26 Drawing Figures

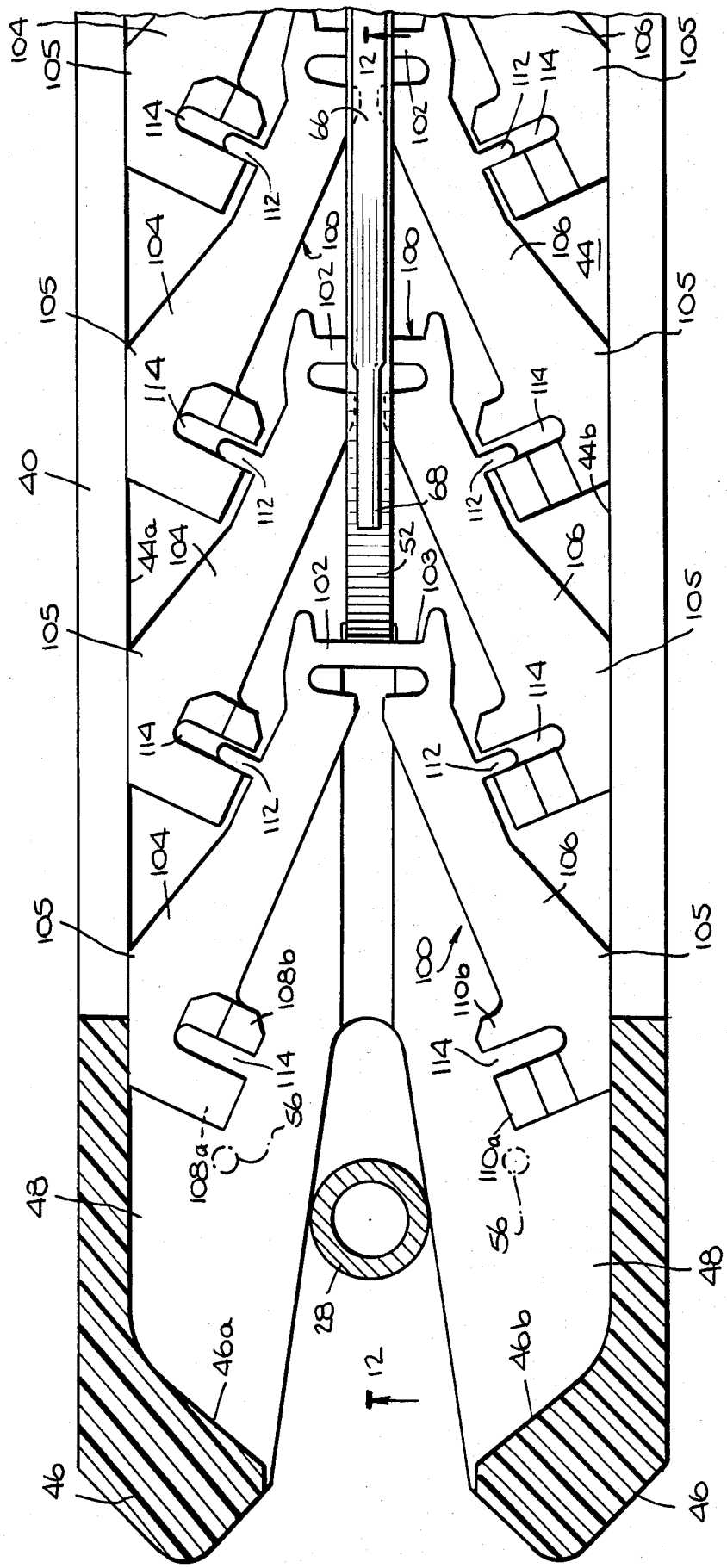

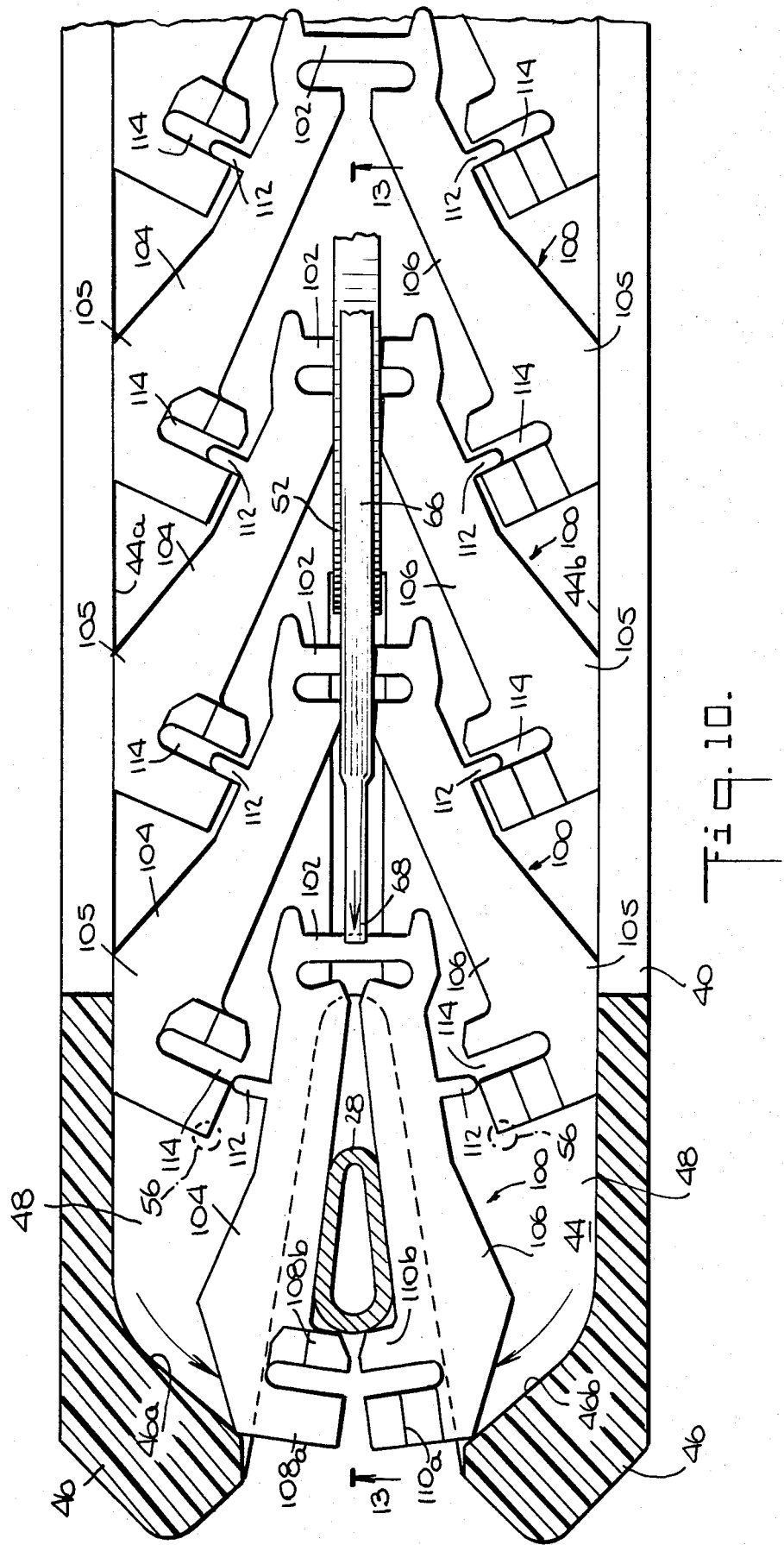

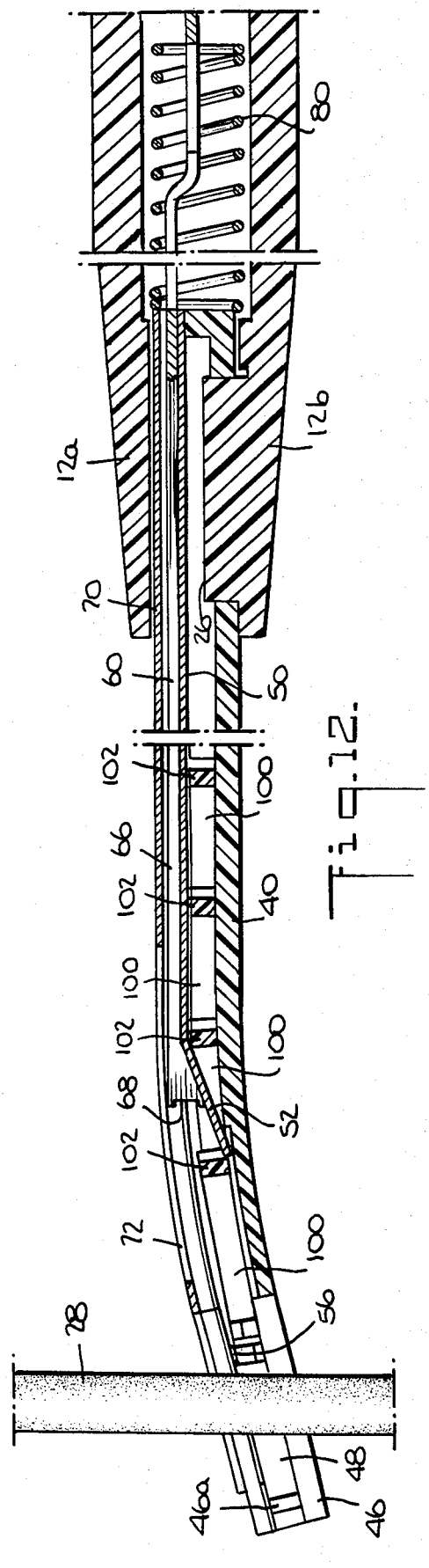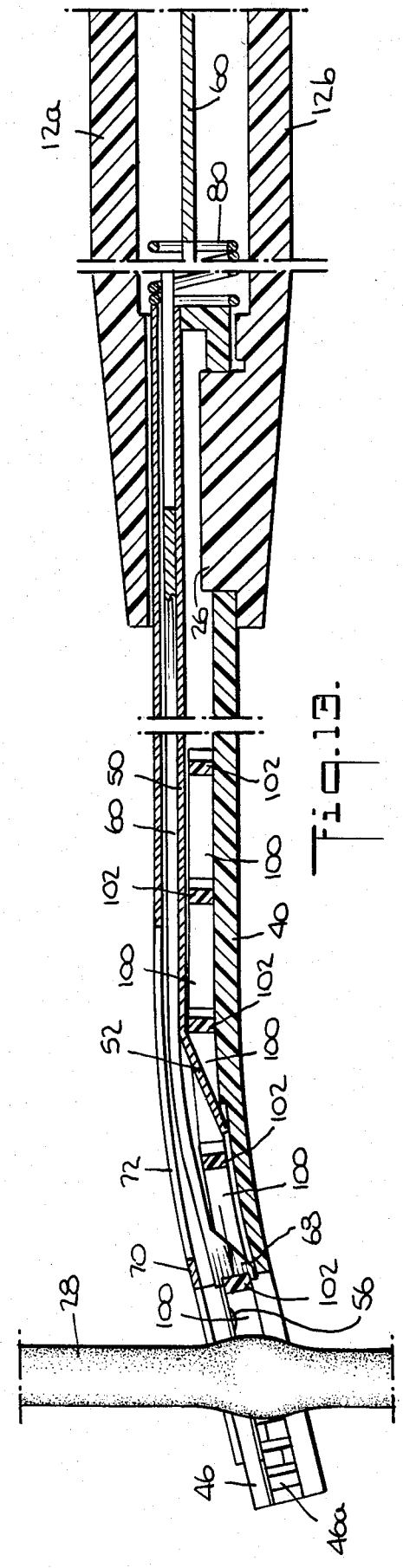

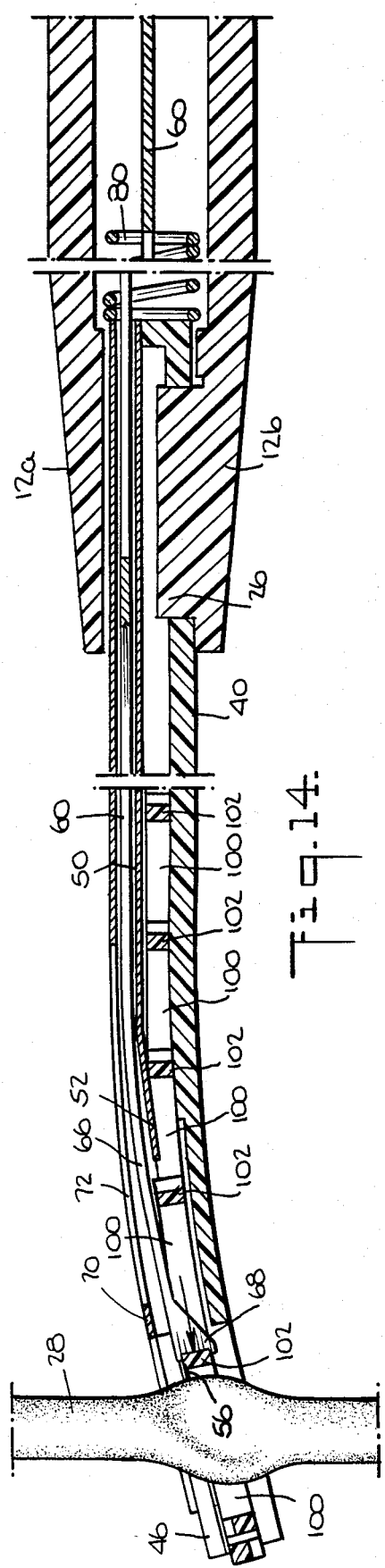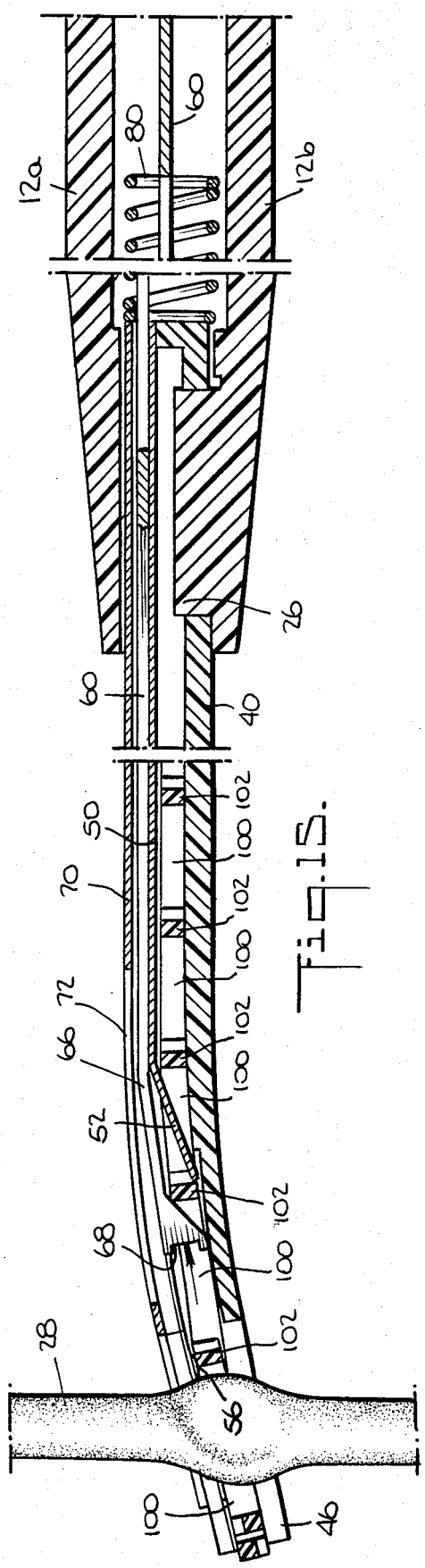

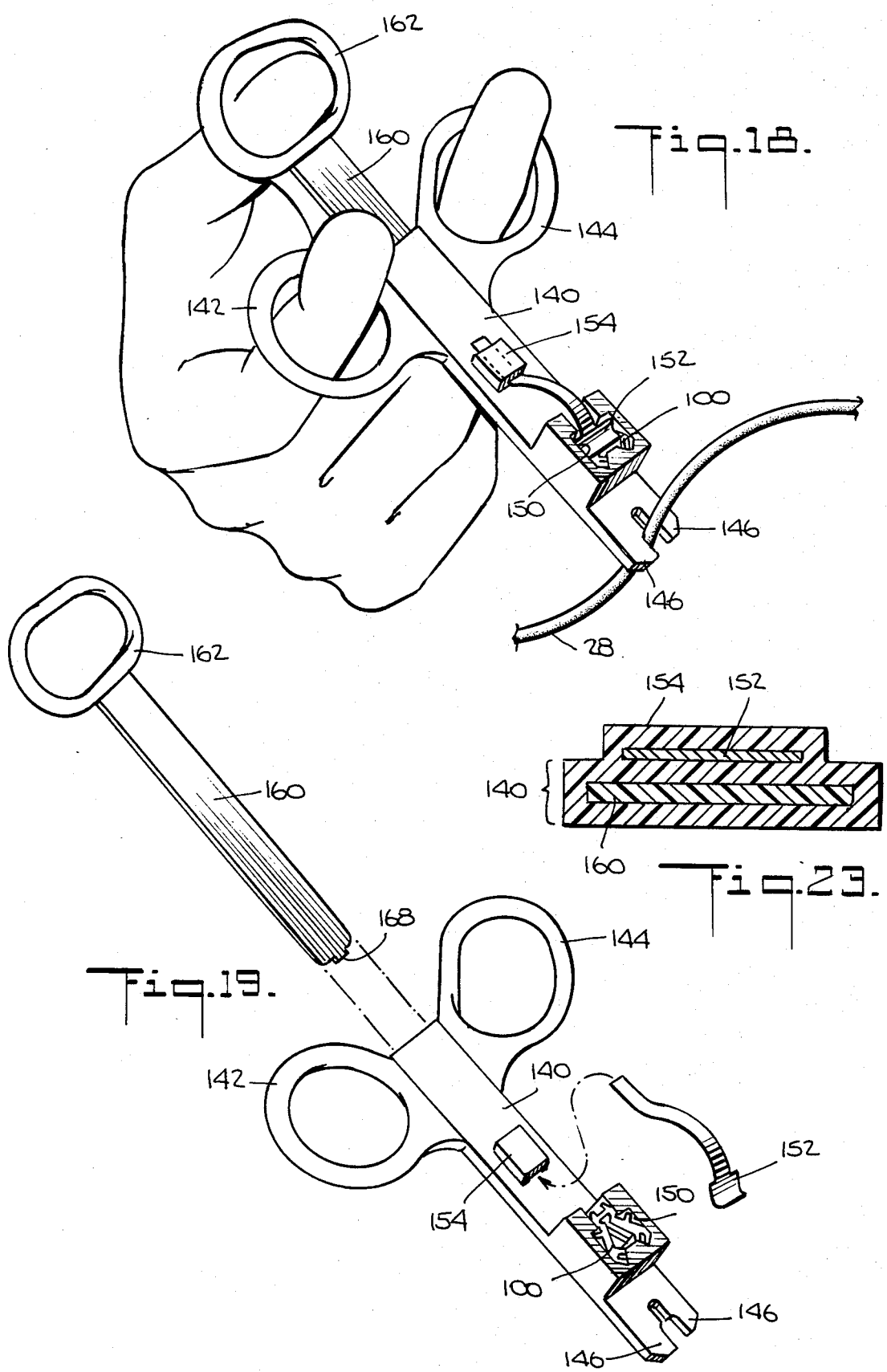

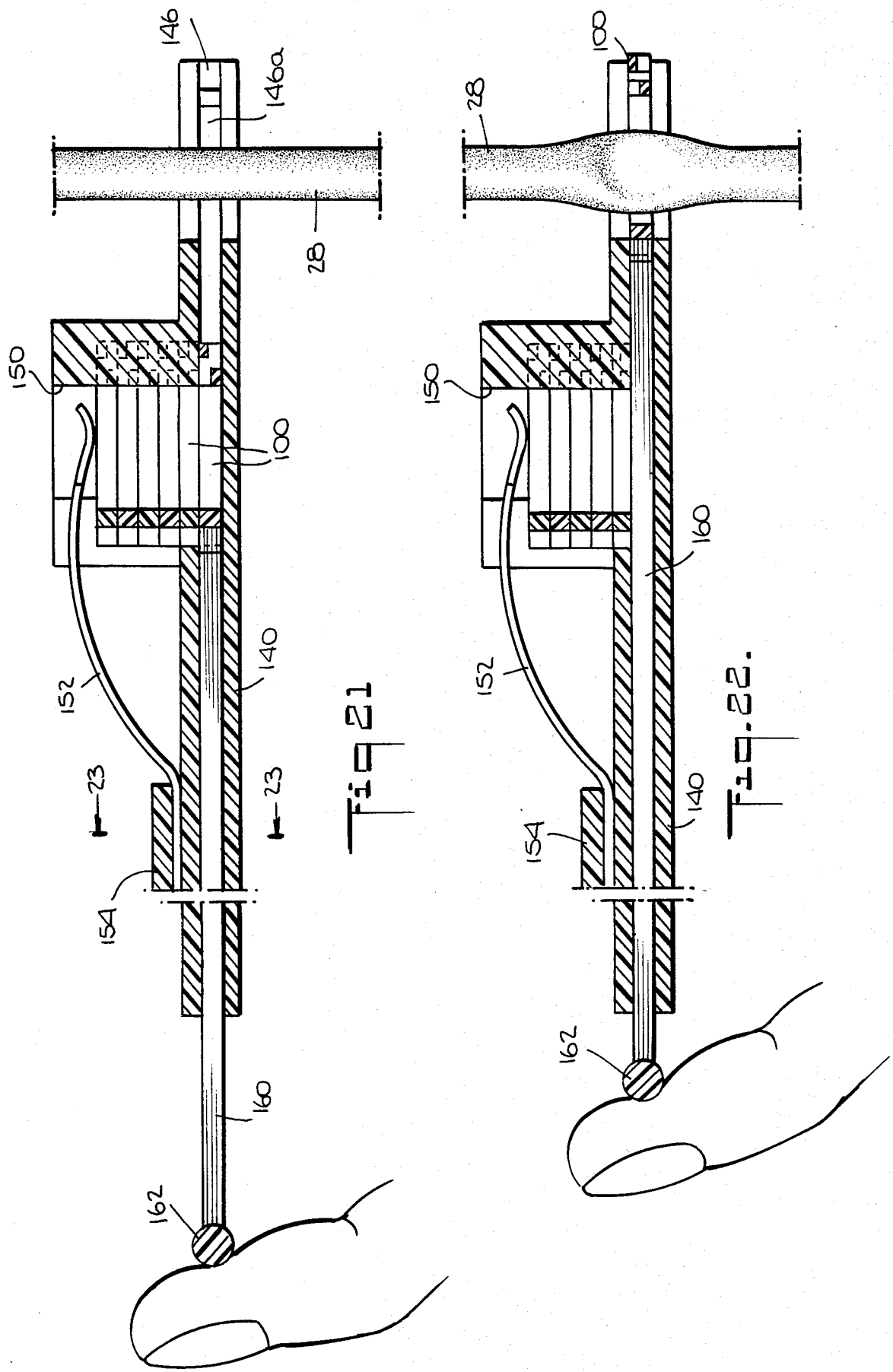

SURGICAL CLIP APPLYING APPARATUS HAVING FIXED JAWS

BACKGROUND OF THE INVENTION

This invention relates to hemostatic surgical clip applying apparatus, and more particularly to hemostatic surgical clip applying apparatus in which clips contained in the apparatus are automatically fed one at a time to a clip closing portion of the apparatus as the apparatus is operated.

Surgical clip applying instruments typically have a pair of laterally spaced, relatively movable jaws for receiving a clip to be applied to body tissue and for subsequently closing the clip on the tissue by bringing the jaws together. The jaws are generally closed by either a pliers-type actuator or by a sleeve which reciprocates toward the jaws and cams them closed. In either case, a substantial number of moving parts is required to move the jaws. This contributes significantly to the cost of the instrument. In addition, a heavier and bulkier instrument construction may be required to provide jaw closing members of sufficient strength to transmit relatively large jaw-closing forces from a proximal actuator to the distal jaws. For example, if the jaws close by pliers-like actuation, two relatively heavy members extending the entire length of the instrument are required to transmit the bending moments needed to close the jaws. The large amount of material required in these members not only increases the cost of the instrument, but also tends to make the instrument bulkier, thereby possibly interfering with the operator's view of the jaws during the application of clips. This can be a major disadvantage in delicate surgical procedures.

Instrument cost is an increasingly important consideration because there is a growing demand for surgical instruments, such as clip applicators, which can be economically discarded after use in a single surgical procedure. This completely avoids all difficulty and expense associated with cleaning, sterilizing, and reloading the apparatus for reuse in another surgical procedure.

There is also growing interest in the use of plastic surgical clips, and especially plastic surgical clips of biologically absorbable material. If left in the body after a surgical procedure, plastic clips do not scatter X-rays and thereby degrade the quality of subsequent radiographs the way metal clips may. And biologically absorbable plastic clips are completely absorbed by the body after the clipped tissue heals, thereby avoiding such possible problems as undesirable migration of clips in the body during the months and years following the surgical procedure.

In view of the foregoing, it is an object of this invention to improve and simplify surgical clip applying apparatus.

It is a more particular object of this invention to provide surgical clip applying apparatus which has fixed clip-closing jaws so that most or all of the moving parts otherwise needed for closing the jaws can be eliminated.

It is still another more particular object of this invention to provide surgical clip applying instruments which are especially suitable for applying plastic surgical clips of either absorbable or nonabsorbable material.

SUMMARY OF THE INVENTION

These and other objects of the invention are accomplished in accordance with the principles of the invention by means of clip applying apparatus having a pair of laterally spaced, fixed jaws for receiving body tissue to be clipped between the jaws, and means for advancing a plurality of clips, one at a time in succession, into the jaws for closing on the body tissue by the jaws. The jaws have opposing surfaces which converge toward one another in the distal direction, and each clip has a base and two arms mounted on respective opposite ends of the base and initially diverging from one another in the distal direction. When a clip is advanced into the jaws, the diverging ends of the arms of the clip respectively contact the converging surfaces of the jaws so that the clip is closed by the jaws. The geometries of the jaws and the clips are preferably such that the arms of a clip closed by the jaws are substantially parallel and sufficiently close together along the entire length of the arms so that the clip provides hemostasis of tissue engaged anywhere between the arms. If plastic clips are used, the normally free ends of the clip arms (i.e., the ends of the arms remote from the clip base) preferably have portions which interlock as the jaws close the clip, thereby permanently holding the clip in the closed condition. Various means may be employed for feeding the clips to the jaws. In a particularly preferred embodiment the surgical clips are releasably coupled to one another in a linear array or train which is advanced toward the jaws by a pusher acting on the distal-most clip in the train. The distal-most clip uncouples from the clip train as the jaws close the clip, and the pusher then retracts behind the next succeeding clip in the train to prepare the apparatus for another cycle of operation in which that next clip will be the distal-most clip.

Further features of the invention, its nature and various advantages will be more apparent from the accompanying drawing and the following detailed description of the invention.

BRIEF DESCRIPTION OF THE DRAWING

FIGS. 3-6 are sectional views taken along the lines 3—3, 4—4, 5—5, and 6—6, respectively, in FIG. 2.

FIG. 7 is a partly exploded perspective view of the apparatus of FIGS. 1-6.

FIG. 8 is a further exploded perspective view of the apparatus of FIGS. 1-7.

FIGS. 9-11 are sectional plan views of a portion of the apparatus of FIGS. 1-8 showing sequential stages in the operation of that apparatus.

FIGS. 12-14 are sectional views taken respectively along lines 12—12, 13—13, and 14—14 in FIGS. 9-11.

FIG. 15 is a view similar to FIGS. 12-14, but showing a further stage in the operating cycle of the apparatus.

FIG. 16 is a perspective view of an illustrative clip used in the apparatus of FIGS. 1-15. The clip is shown in position for application to body tissue but with the surrounding clip applying apparatus removed.

FIG. 17 is a view similar to FIG. 16 but showing the clip applied to the body tissue.

FIG. 18 is a perspective view of another illustrative embodiment of the apparatus of this invention.

FIG. 19 is an exploded perspective view of the apparatus of FIG. 18.

FIG. 21 is a longitudinal sectional view of the apparatus of FIGS. 18–20 showing one stage in the operating cycle of that apparatus.

FIG. 22 is a view similar to FIG. 21 showing a subsequent stage in the operating cycle of the apparatus.

FIG. 23 is a cross sectional view taken along the line 23—23 in FIG. 21.

DETAILED DESCRIPTION OF THE INVENTION

Figure 1:
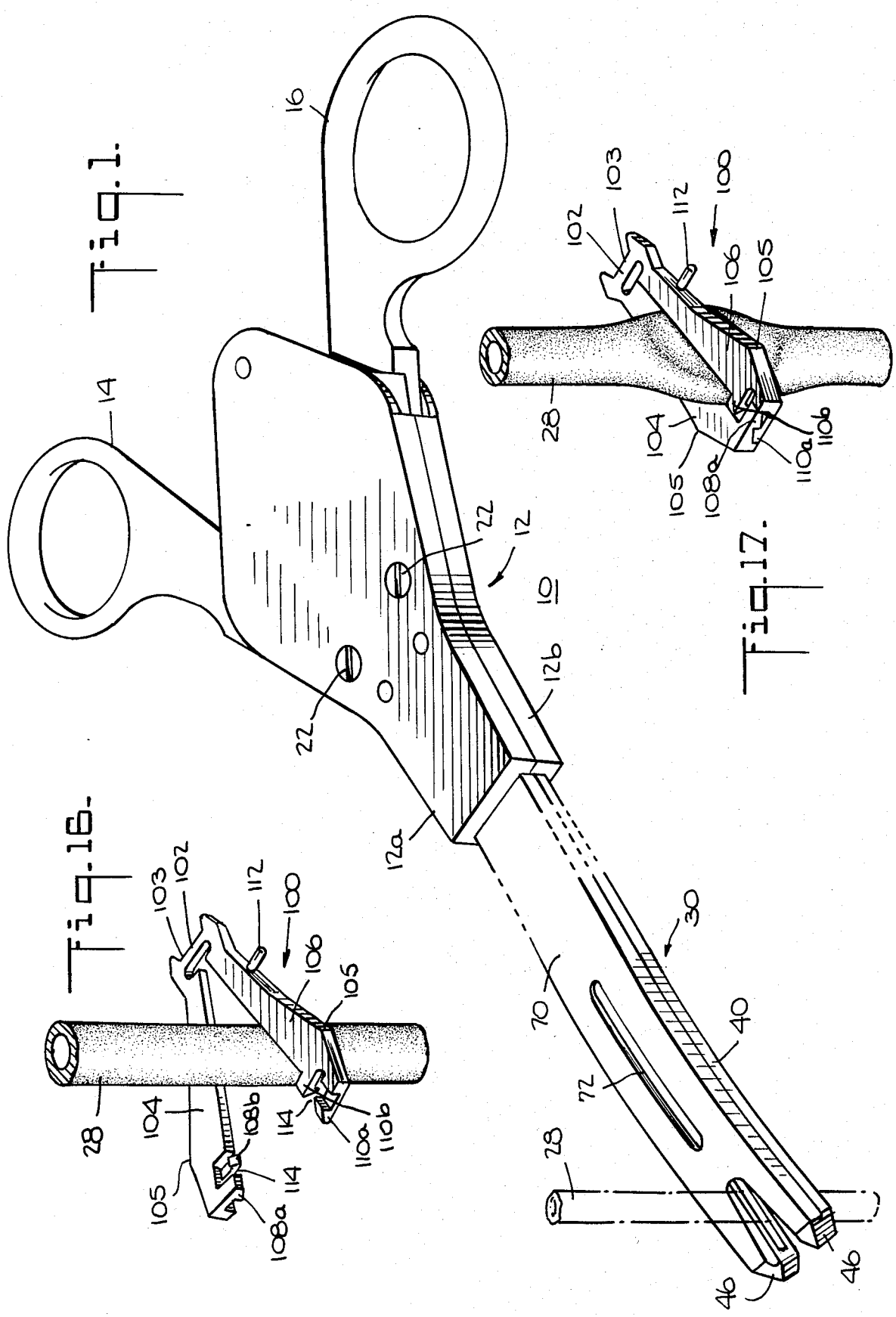
FIG. 1 is a partly foreshortened perspective view of an illustrative embodiment of the surgical clip applying apparatus of this invention.

As shown in FIG. 1, a particularly preferred embodiment of the clip applying apparatus 10 of this invention includes a main body 12 having a pair of proximally (rearwardly) extending ring handles 14 and 16, and a distally (forwardly) extending longitudinal shaft assembly 30. If desired, the distal end portion of shaft assembly 30 may be curved to suit the convenience of the surgeon in applying clips. As best seen in FIG. 7, main body 12 is made up of upper and lower parts 12a and 12b, respectively. When the instrument is assembled, main body parts 12a and 12b are held together by any conventional means such as adhesive between the mutually contacting peripheral surfaces.

Ring handles 14 and 16 are each mounted for pivotal motion in main body 12 by means of a substantially cylindrical knob 18 (FIGS. 2 and 7) at the distal end of each ring handle, in cooperation with cylindrical sockets 20 in the interior of main body 12. If desired, a pin or screw 22 may be located coaxially in each of the above-described pivotal connections so as to extend through main body 12 and the associated knob 18 to help maintain handles 14 and 16 in main body 12. Ring handles 14 and 16 are designed to respectively receive the thumb and a finger of one hand of the surgeon so that the apparatus can be held and operated entirely by one hand, like a pair of scissors. Ring handles 14 and 16 are shown in their position of maximum separation in FIGS. 1 and 2. A clip is applied as described in detail below by squeezing ring handles 14 and 16 together.

Figure 2:
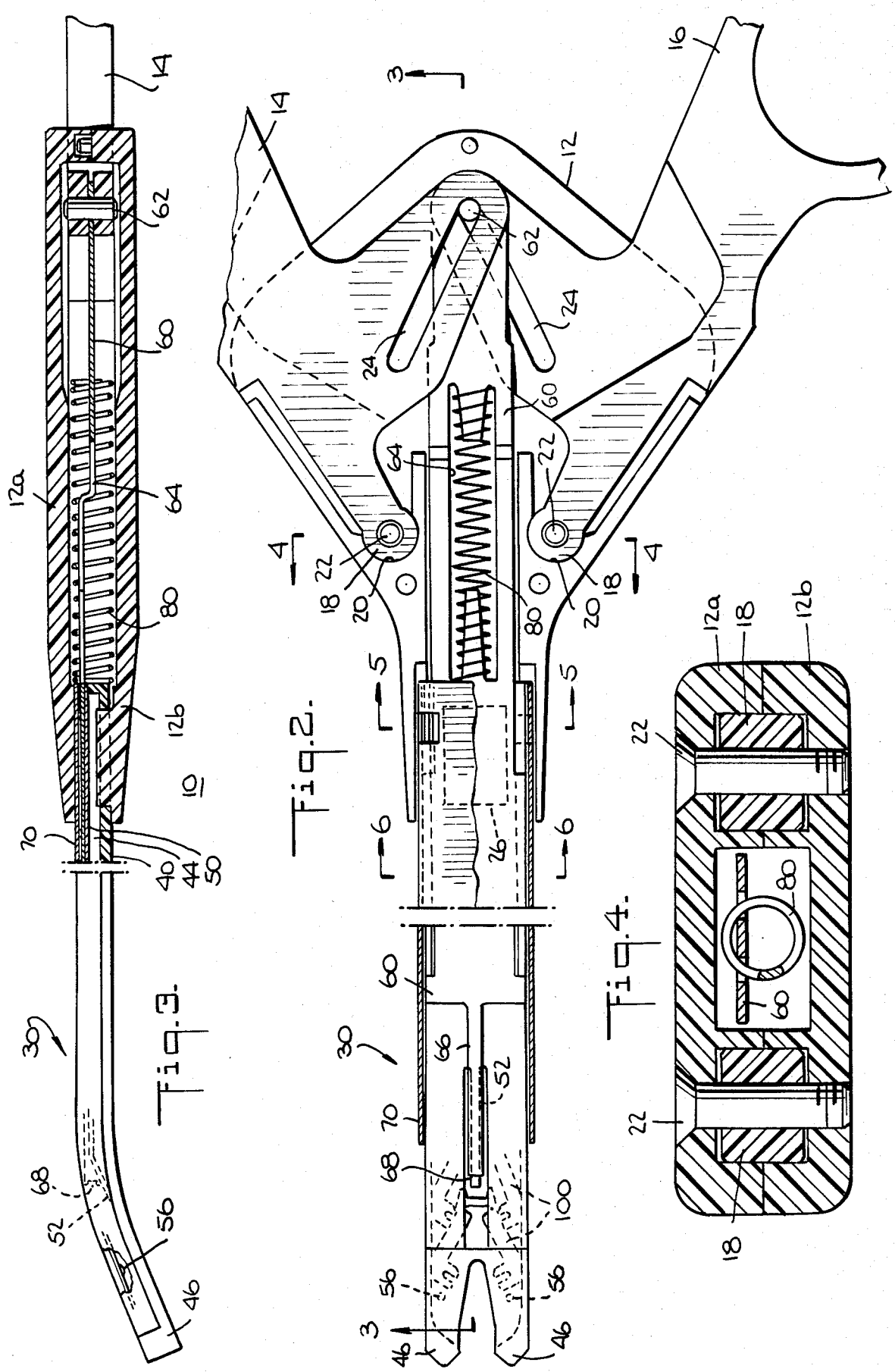
FIG. 2 is a partial plan view of the apparatus of FIG. 1 with part of the cover removed to reveal the interior of the apparatus and with some parts in section.

Each of ring handles 14 and 16 includes an elongated pin driving slot 24 (FIGS. 2 and 7). The portions of handles 14 and 16 defining pin driving slots 24 overlap one another so that the two pin driving slots also overlap. The respective opposite ends of pin 62, which is mounted near the proximal end of pusher member 60, project into slots 24 where they overlap. When ring handles 14 and 16 are squeezed together as described in more detail below, slots 24 cooperate to drive pin 62 in the distal direction.

As best seen in FIG. 8, the components of shaft assembly 30 include jaw member 40, clip train cover 50, pusher member 60, and cover 70. Jaw member 40 is fixedly attached to main body 12 by cooperation of rectangular main body pin 26 and jaw member aperture 42. Jaw member 40 defines a longitudinal clip-holding channel 44. Clip-holding channel 44 contains a plurality of surgical clips 100 arranged in a linear array or train described in more detail below. The distal end of jaw member 40 defines a pair of laterally spaced jaws 46. Body tissue 28 (FIG. 1) to be clipped is positioned between jaws 46, and then the distal-most clip in the clip train is pushed distally into jaws 46. Jaws 46 cooperate with one another to close the clip on the tissue.

Clip train cover 50 is stationarily mounted on jaw member 40 so that it covers clip-holding channel 44. Thus clips 100 move in channel 44 between jaw member 40 and clip train cover 50. The distal end portion of clip train cover 50 includes pawl member 52 which extends downwardly into the central portion of clip-holding channel 44 to allow clips 100 to move in the distal direction in channel 44, but to substantially prevent the clips from moving back in the proximal direction. Pawl member 52 is resiliently biased against the bottom of channel 44.

Figure 3:
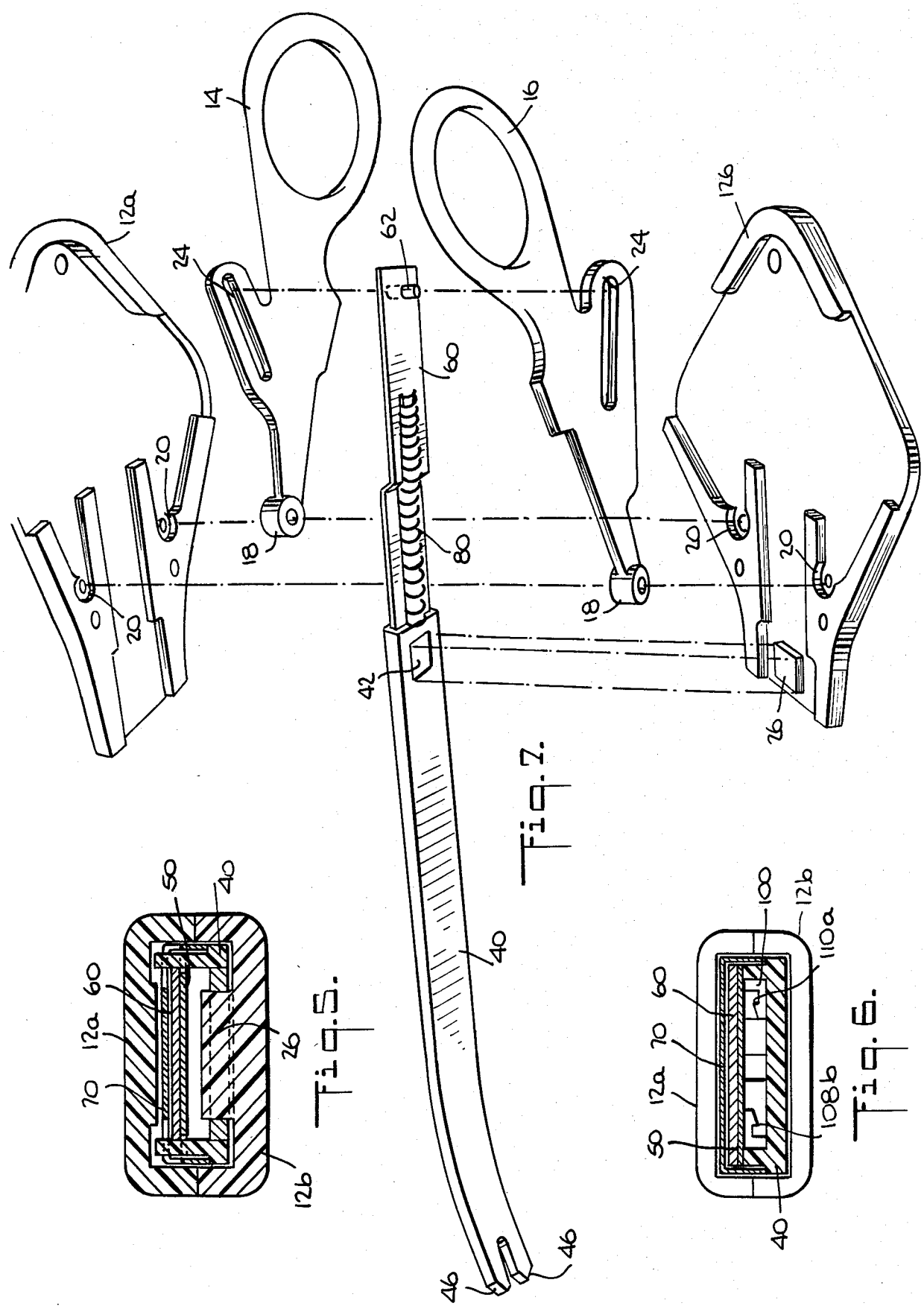
Figure 4:
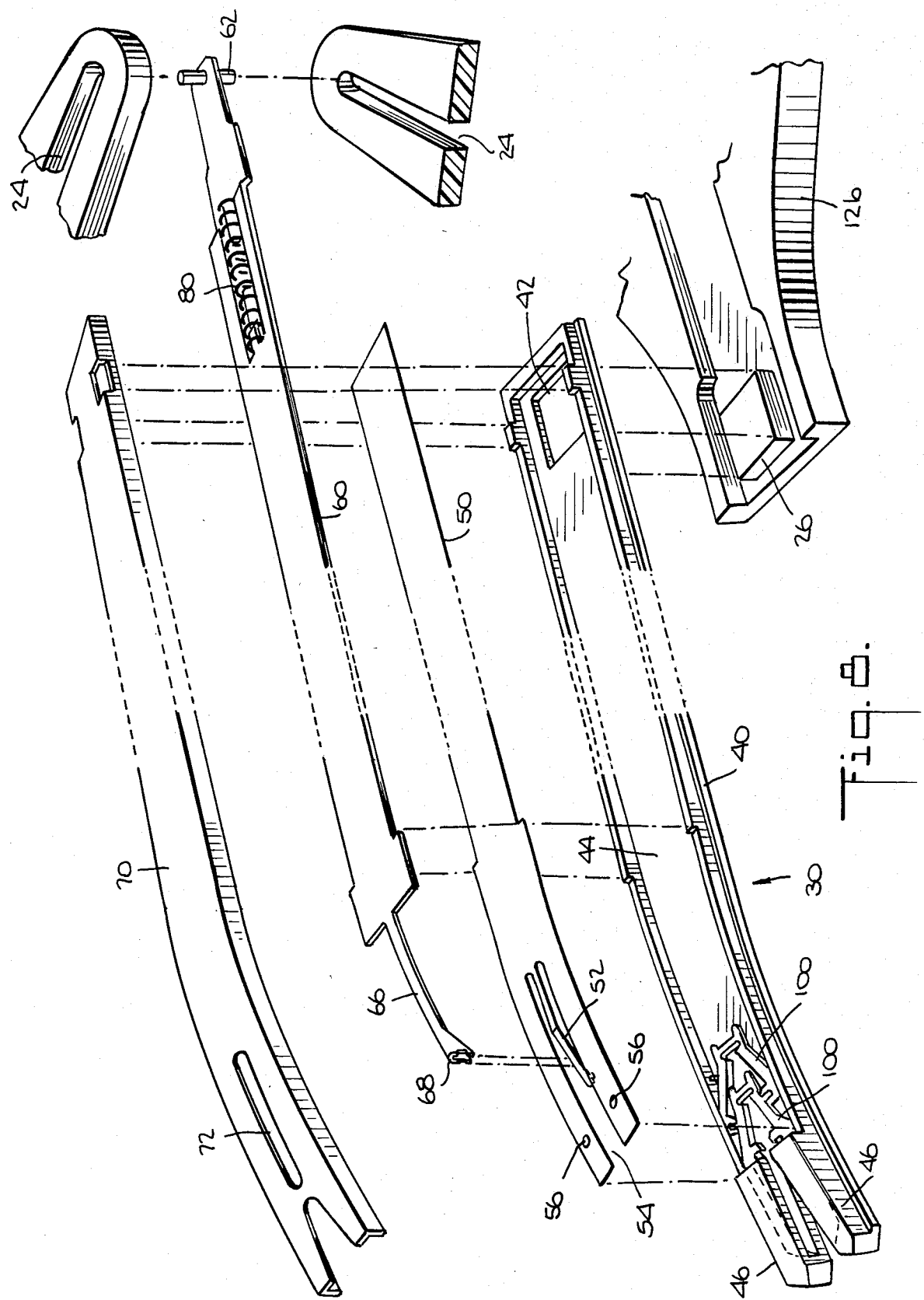

Pusher member 60 is mounted for longitudinal reciprocal motion in shaft assembly 30 between clip train cover 50 and shaft assembly cover 70. Pusher member 60 is resiliently biased in the proximal direction by compression coil spring 80, which is disposed in slot 64 in pusher member 60 and which acts between the proximal end of slot 64 and the proximal end of the stationary elements of shaft assembly 30 (see especially FIG. 3). The distal end of pusher member 60 includes a distally extending leaf spring section 66 which terminates in the actual clip pusher 68. Leaf spring section 66 resiliently biases pusher 68 down in the central portion of channel 44 through a longitudinal slot 54 in clip train cover 50. As described in more detail below, pusher 68 acts on the base 102 of the distal-most clip 100 in the train of clips in clip-holding channel 44 to push that clip into jaws 46. The proximal end portion of pusher member 60 is sandwiched between the overlapping slotted portions of ring handles 14 and 16 described above. Pin 62 extends through pusher member 60 and into handle slots 24 as also described above. The resilient proximal bias of pusher member 60, produced by spring 80, resiliently biases ring handles 14 and 16 apart. Spring 80 is therefore the return spring of the apparatus.

Shaft assembly cover 70 is stationarily attached to jaw member 40 so that it covers pusher member 60. Slot 72 near the distal end of cover 70 allows pusher elements 66 and 68 to flex upwardly during the return stroke of the apparatus as described below.

Although clips 100 may be made of other suitable materials such as metal, in the embodiment being described clips 100 are preferably made of plastic material, most preferably biologically absorbable plastic material. Suitable biologically absorbable plastic materials include homopolymers and copolymers of glycolide, lactide, and p-dioxanone. Suitable nonabsorbable plastic materials include nylon, polyester, and polypropylene.

Figure 11:
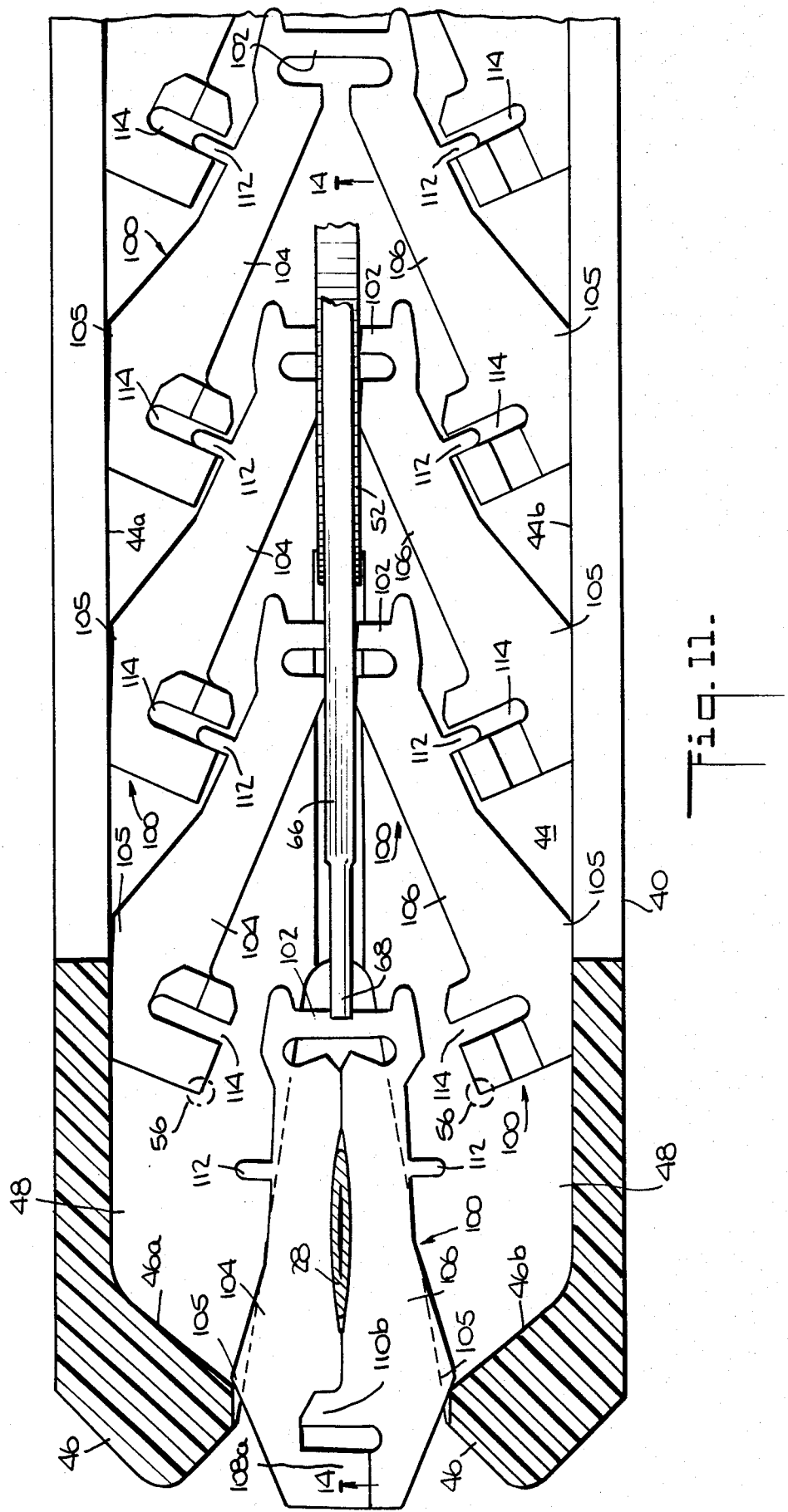
Figure 20:
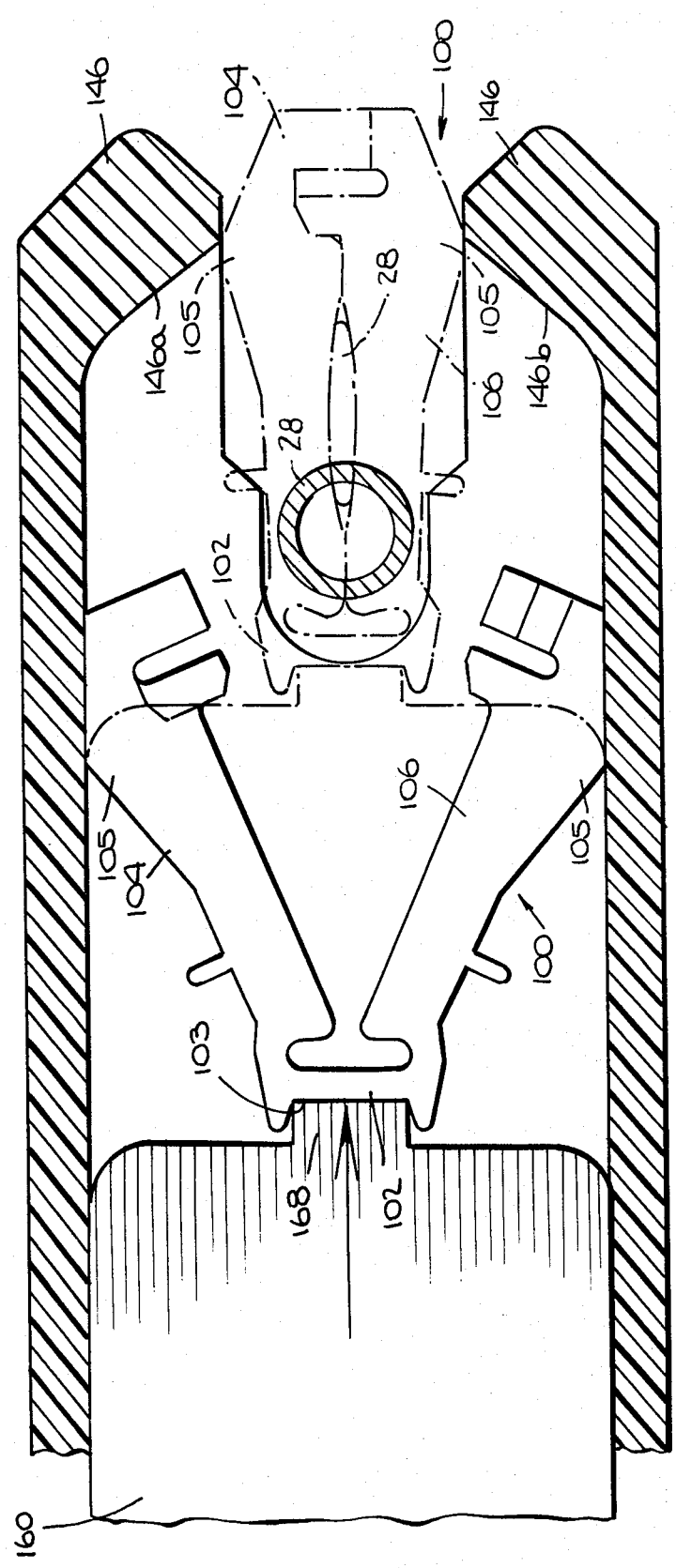
FIG. 20 is a sectional plan view of a portion of the apparatus of FIGS. 18 and 19.

Individual clips 100 are best seen in FIGS. 16 and 17, and the clip train is best seen in FIGS. 9–11. Each clip includes a base 102 and two arms 104 and 106 attached to the respective opposite ends of the base. The proximal side of base 102 is recessed at 103 to receive pusher 68. Both arms lie on the same side of the base, and the base and arms collectively define a plane (i.e., the plane of the paper in FIGS. 9–11). The arms 104 and 106 of each clip initially form equal and opposite obtuse angles with the base 102 of the clip so that the arms are initially spaced apart and diverge from one another in the distal direction in channel 44. The material and construction of the clip is sufficiently flexible that arms 104 and 106 can be brought together in the jaws 46 of the clip applying apparatus.

The initially free end portion of each clip arm 104 and 106 includes latching elements 108a and 108b in the case of arm 104, and 110a and 110b in the case of arm 106. Latching elements 108a and 108b respectively overlap and interlock with latching elements 110a and 110b as best seen in FIG. 17 to hold the clip closed after the arms of the clip have been brought together by jaws 46. It should be noted that the direction of overlap of latching elements 108a and 110a is opposite the direction of overlap of latching elements 108b and 110b. Thus as viewed in FIG. 17, for example, latching element 108a is above element 110a, whereas latching element 110b is above element 108b. Clip 100 therefore strongly resists inadvertent reopening even if the arms of the clip are twisted relative to one another.

Each clip 100 also includes coupling elements 112 and 114 for releasably coupling the physically separate clips together in a linear array or train. The coupling elements 112 of each clip releasably couple with the coupling elements 114 of the succeeding (i.e., following) clip in the train. Although those skilled in the art will recognize that other coupling element configurations are possible and within the scope of the invention, in the particular embodiment shown, coupling elements 112 comprise lugs extending laterally outward from the outer periphery of clip 100, preferably at an intermediate point along the length of arms 104 and 106, and coupling elements 114 comprise slots on the inner periphery of arms 104 and 106 near the initially free ends of the arms. When the clips are assembled in a train as shown, for example, in FIG. 9, the lugs 112 on arms 104 and 106 of each clip respectively project into the slots 114 in arms 104 and 106 of the succeeding clip in the train. The side walls 44a and 44b of clip-holding channel 44 prevent the arms of each clip from spreading apart any farther than shown. Accordingly, all the clips are coupled together so that when the distal-most clip is pushed in the distal direction, each clip pulls along with it the succeeding clip in the train. Thus all the clips move together in the distal direction when the distal-most clip is pushed in that direction.

Clips 100 may have various sizes depending on their intended use. Typical clips may be about 10 mm long and 8 mm wide before being closed. Much smaller clips may be used for certain applications in microsurgery. Larger clips may be used for other purposes such as closing oviducts and vas deferens. The clip applying apparatus is sized appropriately for the clips it is to apply.

Operation of the apparatus is best described with reference to FIGS. 9–15. FIGS. 9–11 depict successive stages in the operating cycle of the apparatus. These same stages are also respectively shown in FIGS. 12–14. FIG. 15 shows a further stage in the operating cycle. The initial condition of the apparatus is shown in FIGS. 9 and 12. A plurality of clips 100 are coupled together in a train as described above and disposed in channel 44 in jaw member 40 with the open side of each clip facing in the distal direction toward jaws 46. The base 102 of the distal-most clip in the train is on the distal side of pawl member 52. The bases of all the other clips are on the proximal side of pawl member 52. Pusher member 60 is in its proximal-most position so that handles 14 and 16 are at their maximum separation as shown in FIGS. 1 and 2. Pusher 68 is resting on pawl member 52 and is therefore also on the proximal side of the base 102 of the distal-most clip.

When it is desired to apply a clip, the body tissue 28 to be clipped is positioned between jaws 46 as shown in FIGS. 9 and 12, and ring handles 14 and 16 are squeezed together. As ring handles 14 and 16 begin to be squeezed together, slots 24 in the ring handles cooperate with pin 62 to begin to drive pusher member 60 in the distal direction as shown in FIGS. 10 and 13. Return spring 80 is gradually compressed during the distal stroke of pusher member 60. As pusher member 60 moves distally, pusher 68 rides down pawl member 52, contacts the proximal side of the base 102 of the distal-most clip 100, and pushes that clip in the distal direction along channel 44. The distal end of pusher 68 is received in recess 103 to help prevent the clip from rotating about an axis perpendicular to the plane of the paper in FIG. 10 as the clip is advanced toward jaws 46. Each arm 104, 106 of the distal-most clip enters a respective one of jaws 46 so that an arm of the clip is on each side of body tissue 28. Each of jaws 46 has a longitudinal channel 48 for receiving and guiding an arm of a clip. Channels 48 keep the clip in the proper orientation in the apparatus until the clip has been closed. All of the other clips in the train are pulled along with the distal-most clip at least until the base of the next-to-distal-most clip has passed under pawl member 52 and is on the distal side of that member as best seen in FIG. 13.

As the base of the next-to-distal-most clip passes pawl member 52, the distal-most portions of the initially free ends of the arms of the distal-most clip begin to contact converging surfaces 46a and 46b near the distal ends of jaws 46 as best seen in FIG. 10. This causes arms 104 and 106 to begin to deflect or pivot toward one another so that the clip begins to close on tissue 28. As arms 104 and 106 converge toward one another, lugs 112 on the distal-most clip disengage from slots 114 in the next-to-distal-most clip, thereby uncoupling the distal-most clip from the remaining clips in the train. Also at this time, portions of the next-to-distal-most clip contact raised clip-retarding dimples or detents 56 on the bottom of clip track cover 50. (The relative longitudinal location of detents 56 is shown in phantom lines in FIGS. 9–11.) Detents 56 project down into channel 44 to contact the next-to-distal-most clip and thereby releasably retard the distal motion of that clip. This helps to uncouple and separate the distal-most clip from the clip train. Further distal motion of pusher 68 advances only the distal-most clip. The remainder of the clip train now remains substantially stationary as a result of the next-to-distal-most clip being held between detents 56 and pawl member 52.

As ring handles 14 and 16 continue to be squeezed together, pusher 68 continues to push the distal-most clip farther into jaws 46. Converging jaw surfaces 46a and 46b continue to force the arms of the distal-most clip together. The outer periphery of each arm preferably includes an outwardly projecting portion 105 for contacting surfaces 46a and 46b during at least a portion of the clip closing stroke of the apparatus to help cam the clip closed. When the apparatus reaches the condition shown in FIGS. 11 and 14, the clip is fully closed and latching elements 108a and 108b respectively interlock with latching elements 110a and 110b to hold the clip closed. Preferably, the closed clip exerts sufficient pressure on the tissue to provide hemostasis without causing undue tissue damage.

The operator now releases the squeezing pressure on ring handles 14 and 16. This allows return spring 80 to drive pusher member 60 back in the proximal direction as shown in FIG. 15. The formerly next-to-distal-most clip, which is now the distal-most clip, is substantially prevented from moving in the proximal direction by pawl member 52. Pusher 68 rides up over the base of the new distal-most clip and then drops down on pawl member 52 on the proximal side of that clip so that the apparatus is restored to the initial condition shown in FIGS. 9 and 12. The apparatus is now ready to begin another cycle of operation. Thus pusher 68 is limited to motion between (1) a proximal-most position in which pusher 68 is between the distal-most clip and the next-to-distal-most clip in the clip train at the location at which the clip train was left when the previously distal-most clip was uncoupled from the clip train, and (2) a distal-most position in which the distal-most clip is fully pushed into jaws 46. In this way one, and only one, clip is pushed into jaws 46 during each operating cycle of the apparatus. The travel of pusher 68 is confined to these limits by the length of pin driving slots 24 in handles 14 and 16.

The clipped tissue can be removed from jaws 46 any time after the clip has been closed. The closed clip and the adjacent jaw structure are sufficiently resilient that the slight interference between the clip and the distal ends of the jaws (see FIG. 11) can be easily overcome to allow the clip and the tissue to be pulled out of the distal end of the apparatus. When plastic clips are used, the jaws may also be made of plastic.

The apparatus of FIGS. 1-17 is especially well adapted for applying plastic clips because the pusher operates on the distal-most clip and the entire clip train therefore does not have to transmit the force required to advance and close the distal-most clip.

It is to be understood that other forms of clip feeding mechanisms can be used with the fixed clip-closing jaws of this invention. FIGS. 18-23 show an alternative embodiment of the invention in which clips are fed one at a time from a stack. The apparatus of this embodiment includes jaw member 140 and pusher member 160 mounted for longitudinal reciprocal motion inside jaw member 140. The proximal end of jaw member 140 includes two finger rings 142 and 144, each of which receives a finger of one hand of the operator of the device as shown in FIG. 18. The proximal end of pusher member 160 includes thumb ring 162. Pusher member 160 is advanced in the distal direction by moving the thumb toward the two fingers holding finger rings 142 and 144. Pusher member 160 is retracted in the proximal direction by moving the thumb away from the fingers holding the finger rings.

The distal end of jaw member 140 includes two laterally spaced fixed jaws 146, which may be similar to jaws 46 in the previously discussed embodiment. A clip stack channel 150 is provided on one side of jaw member 140 proximal of jaws 146 to hold several clips 100 in a stack. For convenience herein, clips 100 in this embodiment are assumed to be similar to clips 100 in the previously discussed embodiment, although in this embodiment the features of the clip which allow the clips to be coupled together in a train are not used. Leaf spring 152 is mounted on the side of jaw member 140 and acts as a follower to urge the stack of clips in channel 150 downward toward the channel in which pusher member 160 reciprocates. Leaf spring 152 is held in place by retainer member 154.

In operation, the distal end of pusher member 160 is initially on the proximal side of the bottom-most clip in the stack. The tissue 28 to be clipped is placed between jaws 146. Pusher member 160 is then advanced in the distal direction as described above so that the distal end of the pusher member contacts the base 102 of the bottom-most clip in the stack and advances that clip in the distal direction toward jaws 146. Each arm 104, 106 of the clip enters a respective one of the jaws 146 so that converging jaw surfaces 146a and 146b cooperate with the initially free end of the clip arms to close the clip around tissue 28 as shown in broken lines in FIG. 20, and as also shown in FIG. 22. As in the previously discussed embodiment, the distal end of pusher member 160 includes a pusher element 168 which is received in recess 103 in the base of the clip to help prevent rotation of the clip as it is advanced toward jaws 146. The closed clip and clipped tissue can be removed from the distal end of the device any time after the clip has been fully closed. If desired, pusher member 160 may be allowed to move distally beyond the point at which the clip is fully closed to assist in removing the closed clip from the end of the apparatus.

When the distal stroke of pusher member 160 is complete, the pusher member may be retracted in the proximal direction to its initial position. When the distal end of pusher member 160 clears the bottom of the stack of clips in channel 150, spring 152 advances the stack so that the next clip drops into the channel in which pusher member 160 reciprocates. The apparatus is now ready to repeat its operating cycle to apply another clip.

Figure 24:
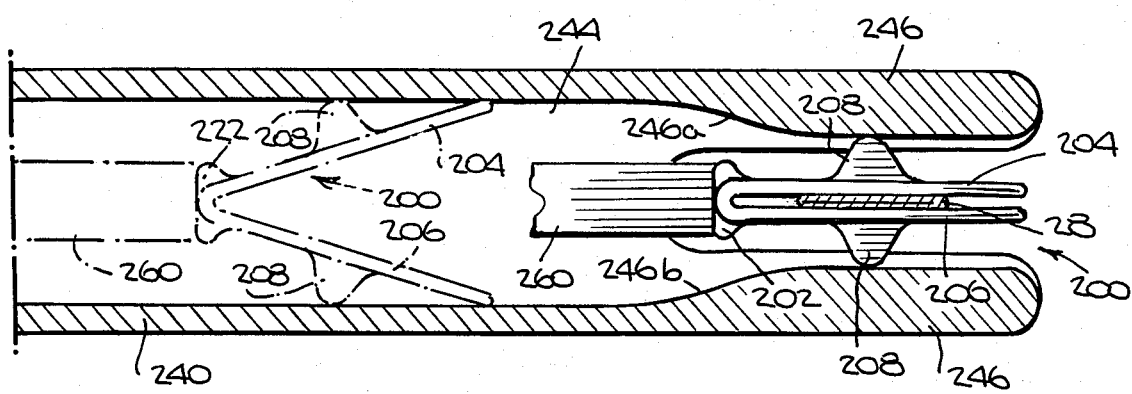
FIG. 24 is a partial sectional view of another alternative embodiment of this invention.
Figure 25:
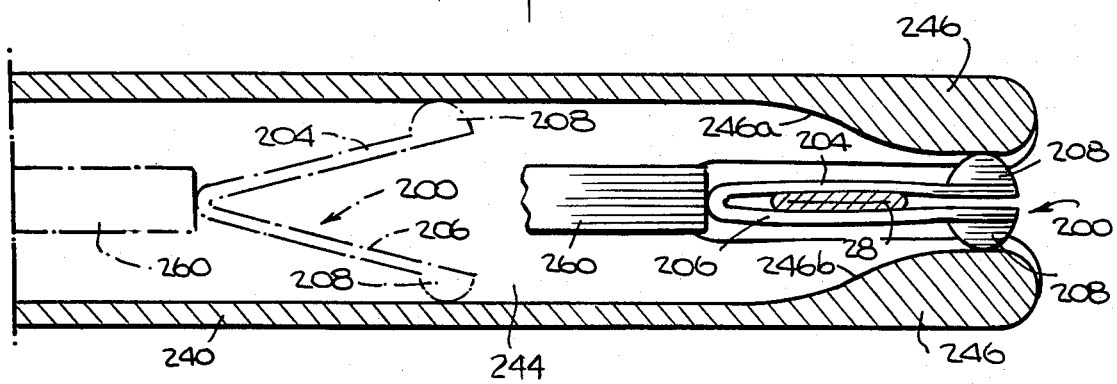
FIG. 25 is a partial sectional view of still another alternative embodiment of this invention.
Figure 26:
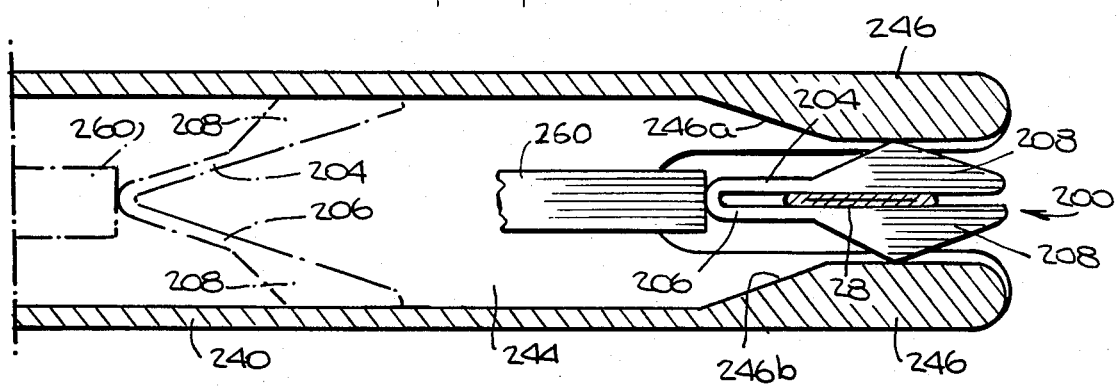
FIG. 26 is a partial sectional view of yet another alternative embodiment of this invention.

Embodiments (like the one just discussed) in which the clips are supplied from a stack are particularly adapted to applying metal surgical clips (i.e., clips of aluminum, magnesium, stainless steel, tantalum and various alloys of these materials (some of which may be biologically absorbable). The metal clips fed in this way can have any of a wide variety of shapes, several of which are illustrated in FIGS. 24-26. In the embodiment shown in FIG. 24, for example, jaw member 240 terminates at its distal end in a pair of laterally spaced fixed jaws 246. A longitudinal channel 244 in jaw member 240 receives a clip 200 at the position shown in broken lines from a stack in a channel (not shown, but generally similar to channel 150 in the embodiment shown in FIGS. 18-23) which is located on the side of the jaw member. Each clip 200 is initially a generally V-shaped structure, preferably of metal, which is oriented in channel 244 with the open side of the V directed toward jaws 246. Clip 200 has a broadened base portion 202 to provide a larger surface for contact by pusher 260. Each arm 204, 206 of clip 200 also has a lug 208 extending laterally outward from an intermediate portion of the arm. Lugs 208 help to stabilize clip 200 in channel 244, and also cooperate with converging jaw surfaces 246a and 246b to complete closing of the clip by jaws 246 as shown in solid lines in FIG. 24. Pusher 260 reciprocates longitudinally in channel 244 in a manner generally similar to pusher 60 in the embodiment of FIGS. 1-17. Any suitable pusher actuator mechanism (not shown) may be used for driving pusher 260. For example, a pusher actuator mechanism similar to that described above in connection with FIGS. 1-17 may be used if desired.

When a clip is to be applied by the apparatus of FIG. 24, the body tissue 28 to be clipped is positioned between jaws 246, and pusher 260 is reciprocated in the distal direction to push clip 200 into the jaws. As clip 200 enters jaws 246, the distal ends of clip arms 204 and 206 first contact converging jaw surfaces 246a and 246b, respectively, to begin to close the clip on the tissue. Thereafter, lugs 208 contact converging jaw surfaces 246a and 246b to complete the closing of the clip as shown in solid lines in FIG. 24. In the fully closed clip (as in the other embodiments shown and described herein), arms 204 and 206 are substantially parallel to one another and close enough together to provide hemostasis of tissue engaged anywhere along the length of the clip. The closed clip is removed from the instrument by sliding it out the distal end of jaw member 240. When pusher 260 is retracted to its initial position, the stack advances to place another clip in front of the pusher. This clip is applied during the next operating cycle of the apparatus.

The embodiments shown in FIGS. 25 and 26 are generally similar in construction and operation to the embodiment shown in FIG. 24, and similar elements have like reference numbers in all of these Figures. In FIGS. 25 and 26, lugs 208 are near the initially free ends of clip arms 204, 206. Thus only lugs 208 contact converging jaw surfaces 246a and 246b to close the clip. In FIG. 25, lugs 208 have semicircular outer peripheral surfaces for contacting jaw surfaces 246a and 246b, while in FIG. 26, lugs 208 have generally triangular outer peripheral surfaces.

It will be understood that the embodiments shown and described herein are merely illustrative of the principles of the invention, and that various modifications can be made by those skilled in the art without departing from the scope and spirit of the invention. For example, in the embodiment of FIGS. 1–17 shaft assembly 30 can be made straight rather than curved as shown in the drawing.

I claim:

1. Apparatus for applying a surgical clip to body tissue to produce hemostatis of the tissue comprising:
    a clip having a proximal base and two arms extending distally from respective opposite ends of the base, each arm including (a) a substantially longitudinal inner surface portion intermediate the base and the distal end of the arm and (b) an outer surface portion which is inclined toward the longitudinal inner surface portion in the distal direction, the longitudinal inner surface portions of the arms initially diverging from one another in the distal direction;
    a longitudinal jaw member having proximal and distal end portions;
    a pair of laterally spaced, relatively fixed jaws mounted on the distal end of the jaw member, each jaw having a clip forming surface which converges in the distal direction toward the clip forming surface of the other jaw;
    channel means aligned with the jaw member for guiding the clip from a proximal portion of the jaw member to the jaws with the diverging ends of the arms oriented toward the jaws; and
    pusher means for pushing the clip through the channel means and into the jaws so that the outer surface portion of each arm contacts a respective one of the clip forming surfaces and the clip forming surfaces cooperate with the outer surface portions to force the longitudinal inner surface portions of the arms together and substantially parallel to one another with the tissue compressed between the longitudinal inner surface portions;
    wherein the clips are releasably coupled to one another in a linear array such that each clip in the array is pulled along by the preceding clip in the array when the preceding clip moves toward the jaws, the array being disposed in and aligned with the channel means, and wherein the pusher means contacts the distal-most clip in the array to push that clip into the jaws and to advance all the other clips in the array toward the jaws.

2. Apparatus for applying a succession of surgical clips to body tissue to produce hemostasis of the tissue, each clip having a base and two arms extending from respective opposite ends of the base and diverging from one another in the direction away from the base, comprising:
    a longitudinal jaw member having proximal and distal end portions;
    a pair of laterally spaced, relatively fixed jaws mounted on the distal end of the jaw member, each jaw having a clip forming surface which converges in the distal direction toward the clip forming surface of the other jaw;
    channel means aligned with the jaw member for guiding the clips one at a time in succession from a proximal portion of the jaw member to the jaws with the diverging ends of the arms oriented toward the jaws; and
    pusher means for pushing the clips one at a time in succession through the channel means and into the jaws so that each arm of the clip being pushed contacts a respective one of the clip forming surfaces and the clip forming surfaces force the arms of the clip together; wherein the clips are releasably coupled to one another in a linear array such that each clip in the array is pulled along by the preceding clip in the array when the preceding clip moves toward the jaws, the array being disposed in and aligned with the channel means; wherein the pusher means contacts the distal-most clip in the array to push that clip into the jaws and to advance all the other clips in the array toward the jaws; wherein a clip can be uncoupled from the succeeding clip in the array by squeezing the arms of the clip together; and wherein the jaws include clip uncoupling surface means for squeezing the arms of the distal-most clip together to uncouple that clip from the succeeding clip as the distal-most clip enters the jaws.

3. The apparatus defined in claim 2 further comprising means for releasably retarding the distal-most of the next-to-distal-most clip when the distal-most clip is to be uncoupled.

4. The apparatus defined in claim 3 wherein the means for releasably retarding the distal motion of the next-to-distal-most clip comprises detent means for contacting the next-to-distal-most clip when the distal-most clip is to be uncoupled.

5. The apparatus defined in claim 2 further comprising:
    actuator means for reciprocating the pusher means in the channel means between (1) a proximal-most position in which the distal end of the pusher means is intermediate the distal-most clip in the array and the next-to-distal-most clip in the array, and (2) a distal-most position in which the arms of the distal-most clip have been forced together by the jaws.

6. The apparatus defined in claim 5 further comprising pawl means for substantially preventing the array of clips from moving in the proximal direction in the channel means.

7. The apparatus defined in claim 6 wherein the pawl means comprises a leaf spring disposed in the channel means and aligned with the channel means, the proximal end of the leaf spring being fixedly attached to the apparatus, and the distal end of the leaf spring resiliently projecting into the channel means so that clips can move in the distal direction past the leaf spring by depressing the distal end of the leaf spring, but so that a clip moving in the proximal direction toward the leaf spring is stopped by contact with the distal end of the leaf spring.

8. Apparatus for applying a plurality of surgical clips to body tissue one at a time in succession to produce hemostasis of the tissue comprising:

a plurality of surgical clips in a longitudinal array, each clip having (a) a proximal base, (b) two arms extending distally from respective opposite ends of the base, each arm including (i) a substantially longitudinal inner surface portion intermediate the base and the distal end of the arm and (ii) an outer surface portion which is inclined toward the longitudinal inner surface portion in the distal direction, the longitudinal inner surface portions of the arms initially diverging from one another in the distal direction, and (c) first and second complementary surface portions, the first surface portion of each clip releasably interfitting with the second surface portion of the preceding clip so that the clip is pulled in the distal direction when the preceding clip moves in that direction;

a longitudinal jaw member having proximal and distal end portions;

a pair of laterally spaced relatively fixed jaws mounted on the distal end of the jaw member, each jaw having a clip forming surface which converges in the distal direction toward the clip forming surface of the other jaw;

channel means aligned with the jaw member for guiding the distal-most clip in the array from a proximal portion of the jaw member to the jaws with the diverging ends of the arms of the clip oriented toward the jaws; and pusher means for contacting the distal-most clip in the array and for pushing that clip through the channel means and into the jaws so that the outer surface portion of each arm contacts a respective one of the clip forming surfaces and the clip forming surfaces cooperate with the outer surface portions to disengage the distal-most clip from the succeeding clip and to force the longitudinal surface portions of the arms of the distal-most clip together and substantially parallel to one another with the tissue compressed between the longitudinal inner surface portions.

9. The apparatus defined in claim 8 wherein the portion of the pusher means which contacts the clip and the portion of the clip contacted by the pusher means include cooperating clip stabilizing means for substantially preventing the clip from rotating about an axis perpendicular to the longitudinal axis of the jaw member during the clip pushing stroke of the pusher means.

10. The apparatus defined in claim 9 wherein the clip stabilizing means comprises two laterally spaced proximally extending projections on the portion of the clip contacted by the pusher means, the distal end of the pusher means being received between the projections.

11. Apparatus for applying a plurality of surgical clips to body tissue one at a time in succession comprising:

a plurality of surgical clips in a linear array, each clip including first and second coupling means for respectively releasably interfitting with the second coupling means of the preceding clip and releasably interfitting with the first coupling means of the succeeding clip so that each clip pulls along the succeeding clip when advanced in the direction away from the succeeding clip;

third means disposed adjacent to, but just beyond the forwardmost clip in the array for closing a clip pushed into the third means, the third means comprising a pair of laterally spaced fixed jaws having opposing surfaces which incline toward one another in the direction away from the array of clips for closing the forwardmost clip as it is pushed into the third means; and fourth means for engaging the forwardmost clip, pushing the forwardmost clip into the third means, and uncoupling the forwardmost clip from the succeeding clip as the forwardmost clip enters the third means.

12. The apparatus defined in claim 11 wherein each clip comprises a base adjacent the succeeding clip and two arms attached to opposite ends of the base and extending in the direction of the preceding clip, the free ends of the arms remote from the base being resiliently biased apart, and the base and arms of all of the clips lying in a common geometric surface.

13. The apparatus defined in claim 12 wherein the first coupling means is disposed on the inner surface of the arms and the second coupling means is disposed on the outer surface of the clip.

14. The apparatus defined in claim 12 wherein the clips are made of plastic material and wherein the end portions of the arms remote from the base include sixth means for causing the end portions of the arms to interlock when the clip is closed by the third means.

15. The apparatus defined in claim 14 wherein the clips are made of a biologically absorbable material.

16. The apparatus defined in claim 11 further comprising means for limiting the travel of the fourth means between (1) a rearwardmost position in which the portion of the fourth means which engages the forwardmost clip is between the forwardmost clip and the next-to-forwardmost clip in the array where the array is positioned after the previously forwardmost clip was uncoupled from the array, and (2) a forwardmost position in which the forwardmost clip has been fully pushed into the third means.

17. The apparatus defined in claim 11 further comprising means for allowing the array of clips to move substantially only in the forward direction.

18. The apparatus defined in claim 11 wherein each clip and the portion of the fourth means which engages the forwardmost clip include cooperating clip stabilizing means for substantially preventing the clip engaged by the fourth means from rotating about an axis perpendicular to the axis along which the clip is pushed.

19. Apparatus for applying a plurality of surgical clips to body tissue one at a time in succession comprising:

a plurality of surgical clips in a linear array, each clip including (a) a base adjacent the succeeding clip, (b) two arms attached to opposite ends of the base and extending in the direction of the preceding clip, the free ends of the arms remote from the base being resiliently biased apart, and (c) first and second coupling means for respectively releasably coupling the clip to the second coupling means of the preceding clip and to the first coupling means of the succeeding clip in the array so that each clip pulls along the succeeding clip when advanced in the direction away from the succeeding clip, the first coupling means being disposed on the inner surface of the arms and the second coupling means being disposed on the outer surface of the clip;

third means disposed adjacent to, but just beyond the forwardmost clip in the array for closing a clip pushed into the third means, the third means comprising a pair of laterally spaced fixed jaws having opposing surfaces which inclined toward one another in the direction away from the array of clips for closing the forwardmost clip as it is pushed into the third means; and fourth means for engaging the forward most clip, pushing the forwardmost clip into the thid means, and uncoupling the forwardmost clip from the succeeding clip as the forwardmost clip enters the third means, the fourth means including fifth means for deflecting the arms of the forwardmost clip toward one another to uncouple the forwardmost clip from the succeeding clip.

* * * * *